(12) United States Patent
Kaercher et al.

(10) Patent No.: US 9,387,003 B2
(45) Date of Patent: Jul. 12, 2016

(54) HANDLING DEVICE FOR A MICRO-INVASIVE SURGICAL INSTRUMENT

(75) Inventors: Daniel Kaercher, Radolfzell (DE); Jochen Stefan, Wald (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 230 days.

(21) Appl. No.: 13/443,607

(22) Filed: Apr. 10, 2012

(65) Prior Publication Data
US 2012/0271347 A1 Oct. 25, 2012

(30) Foreign Application Priority Data
Apr. 11, 2011 (DE) .......................... 10 2011 007 121

(51) Int. Cl.
*A61B 17/29* (2006.01)
*A61B 17/00* (2006.01)

(52) U.S. Cl.
CPC .............. *A61B 17/2909* (2013.01); *A61B 17/29* (2013.01); *A61B 2017/0046* (2013.01); *A61B 2017/292* (2013.01); *A61B 2017/293* (2013.01);
(Continued)

(58) Field of Classification Search
CPC ........... A61B 17/29; A61B 2017/0046; A61B 2017/293; A61B 2017/292; A61B 2017/2929; A61B 2017/2903; A61B 17/2909; A61B 17/2841; A61B 17/22031; A61B 17/0483; A61B 17/3201; A61B 17/44; A61B 2017/2912; A61B 2017/2913; A61B 2017/2915; A61B 2017/2916; A61B 2017/2917; A61B 2017/2923; A61B 2017/2924

USPC .............. 606/1, 57, 120, 148, 157, 170, 180, 606/203, 205, 210
See application file for complete search history.

(56) References Cited

U.S. PATENT DOCUMENTS 5,308,358 A * 5/1994 Bond et al. .................... 606/205
5,368,606 A * 11/1994 Marlow et al. ................ 606/170
(Continued)

FOREIGN PATENT DOCUMENTS

DE 19722062 A1 12/1998
DE 19809120 C1 8/1999
(Continued)

OTHER PUBLICATIONS

European Search Report; Application No. EP 12 00 2392; Issued: Jul. 17, 2012; Mailing Date: Jul. 24, 2012; 4 pages.
(Continued)

*Primary Examiner* — Julian W Woo
*Assistant Examiner* — Lucas Paez
(74) *Attorney, Agent, or Firm* — Whitmyer IP Group LLC

(57) ABSTRACT

A handling device for a micro-invasive surgical instrument includes a gripping device to hold and guide the handling device, a shaft coupling to couple the handling device with a proximal end of a shaft, and a rod coupling that can slide linearly inside the handling device between a distal assembly position and a range of working positions for coupling with a proximal end of a transmission rod that can be slid inside a shaft coupled with the shaft coupling. The slidable rod coupling is configured, in the assembly position, to receive or release a proximal end of a transmission rod and to hold a proximal end of a transmission rod, in the range of working positions. The shaft coupling is configured to block a proximal end of a shaft in a position in which the proximal end of the shaft holds the rod coupling in the range of working positions.

8 Claims, 4 Drawing Sheets

(52) U.S. Cl.
CPC . *A61B 2017/2903* (2013.01); *A61B 2017/2912* (2013.01); *A61B 2017/2929* (2013.01)

(56) References Cited

U.S. PATENT DOCUMENTS

| | | | | |
|---|---|---|---|---|
| 5,620,456 | A | * | 4/1997 | Sauer ................. A61B 17/3417 604/164.01 |
| 5,782,834 | A | * | 7/1998 | Lucey et al. .................... 606/22 |
| 2006/0074432 | A1 | * | 4/2006 | Stad et al. ........................ 606/90 |
| 2008/0046001 | A1 | * | 2/2008 | Renger et al. ................. 606/205 |
| 2008/0046003 | A1 | | 2/2008 | Renger et al. |
| 2009/0088599 | A1 | * | 4/2009 | Zook ................. A61B 17/3403 600/29 |
| 2013/0023911 | A1 | * | 1/2013 | Esanu ........................... 606/158 |

FOREIGN PATENT DOCUMENTS

| | | |
|---|---|---|
| DE | 19853305 C1 | 10/2000 |
| DE | 10224190 B3 | 1/2004 |
| DE | 102006038515 A1 | 2/2008 |
| DE | 102006038516 A1 | 2/2008 |
| DE | 102008015418 A1 | 9/2009 |
| DE | 102008052623 A1 | 4/2010 |
| EP | 1005836 A1 | 6/2000 |
| EP | 1622521 B1 | 1/2011 |
| WO | 2009046490 A1 | 4/2009 |

OTHER PUBLICATIONS

DE Search Report Application No. 10 2011 007 121.0 Date: Oct. 25, 2012 5 pages.

* cited by examiner

HANDLING DEVICE FOR A MICRO-INVASIVE SURGICAL INSTRUMENT

CROSS-REFERENCE TO RELATED APPLICATIONS

The present application claims priority of German patent application No. 10 2011 007 121.0 filed on Apr. 11, 2011.

FIELD OF THE INVENTION

The present invention relates to a handling device for a micro-invasive surgical instrument, to a micro-invasive surgical instrument and thereby, in particular, to characteristics for coupling a shaft and a transmission rod with the handling device.

BACKGROUND OF THE INVENTION

Many micro-invasive surgical instruments include a long, thin shaft, a tool on the distal end of the shaft and a handling device on the proximal end of the shaft. The tool includes, for example, a grasping, dissecting, biopsy or other forceps, a scissors or a needle holder with at least two straight or curved clamps, cutting edges or other jaw members of which at least one is movable. Alternatively, the tool includes another active device, for example a manipulator with a finger or a finger-shaped device or an electrode in hook form or other shape. The shaft contains (at least) one transmission rod, which as a rule is mounted in a closed channel in the interior of the shaft. The handling device includes one or more actuation devices that can move with respect to one another, for example two gripping parts, that medical staff can move in relation to one another with one hand. The proximal end and the distal end of the transmission rod are coupled with the actuation device or with the tool in such a way that a force exerted by medical staff onto the actuation devices or a relative movement of the actuation devices caused by medical staff can be transmitted to the tool, for example to move clamps toward one another or to press them together.

In using a micro-invasive surgical instrument of this type, the tool and a part of the shaft are inserted into a natural or artificial cavity in the patient's body, for example through a natural or artificial bodily opening. The development of micro-invasive surgical techniques tends toward using constantly smaller and, especially, fewer means of access. For example, in order to be able to work with an endoscope and two instruments in laparoscopic surgery by way of a single trocar, instruments with curved shafts can be used. An instrument with a curved shaft, however, cannot always be easily rotated around its longitudinal axis inside the access way in order to modify the orientation of the tool at its distal end.

In patent DE 10 2006 038 516 A1, a tubular medical instrument is described in which a tool 5, a shaft 3 and a handle 2 can be separated from one another for cleaning.

Patent DE 10 2008 015 418 A1 discloses a medical instrument with a curved shaft. A jaw member is detachably connected with a shaft by means of a bayonet lock. In connected position, the jaw member can be rotated with respect to the shaft. The shaft is detachably connected with a handle. The curved shaft can be rotated with respect to the handle by means of a hand wheel that is connected with an external shaft tube in torque-proof manner. An inside tube is connected to the handle with an additional hand wheel. The instrument can be configured as a unipolar or bipolar HF instrument.

Patent DE 10 2008 052 623 A1 discloses a surgical instrument with a jaw unit, a shaft and a gripping unit. The jaw unit is detachably affixed to the end of a shaft tube of the shaft and can rotate with respect to it.

To allow easy, thorough cleaning of the instrument, the tool, shaft and handling device of a micro-invasive surgical instrument, without use of auxiliary means, ought to be separable from one another and capable of being combined or coupled with one another. It is known, for example, from DE 10 2006 038 516 A1 how to configure the tool and the distal end of the shaft in such a way that the tool can be assembled and disassembled in a fully open assembled position. However, a few aspects both of the coupling of the tool with the shaft and of the coupling of the shaft with the handling device have not been sufficiently satisfactorily resolved to date, especially concerning the ability of the tool to turn or rotate with respect to the shaft when in coupled state.

BACKGROUND OF THE INVENTION

An object of the present invention consists in providing an improved tool for a micro-invasive surgical instrument and an improved micro-invasive surgical instrument.

This object is fulfilled through the content of the independent claims.

Refinements are indicated in the dependent claims.

Embodiments of the present invention are based on the idea of configuring a handling device with a rod coupling that can be slid between an assembly position and a predetermined proximal range of working positions in such a way that a proximal end of a shaft blocked in a shaft coupling of the handling device directly or indirectly holds the rod coupling in the predetermined range of working positions. A blocking of the proximal end of a shaft in the shaft coupling of the handling device means, in particular, a blocking with respect to a movement of the proximal end of the shaft parallel to its longitudinal axis. The shaft, in particular, can rotate around the longitudinal axis of its proximal end with respect to the handling device even when it is blocked on the handling device.

A handling device for a micro-invasive surgical instrument includes a gripping device for manual holding and guiding of the handling device, a shaft coupling for detachable mechanical coupling of the handling device with a proximal end of a shaft and a rod coupling, which can slide linearly in the handling device between a predetermined distal assembly position and a predetermined proximal range of working positions for detachable mechanical coupling with a proximal end of a transmission rod, which can at least either slide or rotate in a shaft coupled with the shaft coupling, such that the slidable rod coupling is configured in order to receive or release, in the predetermined assembly position, a proximal end of a transmission rod and in order, with the rod coupling in the predetermined range of working positions, to hold a proximal end of a transmission rod that is inserted into the rod coupling, and such that the shaft coupling is configured in order to block a proximal end of a shaft, which is inserted into the shaft coupling, in a predetermined position in which the proximal end of the shaft holds the rod coupling in the predetermined range of working positions.

The rod coupling can slide linearly along a curved or straight path. The straight path, along which the rod coupling can slide, is in particular parallel to a longitudinal axis of a proximal end of a transmission rod, which is inserted into the handling device or is to be inserted into the handling device. It is understood that the longitudinal axis of a shaft, transmission rod or proximal end of a shaft or transmission rod means, in particular, the axis to which the particular object is rotation-symmetrical or essentially rotation-symmetrical. In the case of a curved shaft or of a pliable transmission rod, these comments refer in particular to their ends, which as a rule are straight or not curved, at least in portions.

The rod coupling is configured in particular in order to hold the proximal end of a transmission rod in a form-locked or force-locked connection in the working range. The rod coupling is configured in particular for coupling with a pliable transmission rod. The predetermined range of working positions of the rod coupling is situated, in particular, proximally from the assembly position. The predetermined working range can be extended, in particular extended by several millimeters. Alternatively, the working range can be small or—in the context of the achievable or employed precision—can include only one position. In addition to the aforementioned assembly position, other assembly positions can be foreseen within a connecting interval, in particular, or within a range (assembly range).

The rod coupling, in addition, can rotate around a longitudinal axis of a shaft that is coupled, or is to be coupled, with the handling device.

A handling device as described here is foreseen and configured in particular for use or combination with a transmission rod, at least either to transmit a translational movement and a corresponding push or pull force or to transmit a rotational movement and a corresponding torque to the distal end of the transmission rod.

The proximal end of a transmission rod, for which the handling device is foreseen and configured, can have a cross-section that is constant within a predetermined range. Torque between the orientation device and/or the rod coupling on the one hand and the proximal end of the transmission rod on the other hand can be transmitted by form-locking through a non-rotation-symmetrical cross-section of the proximal end of the transmission rod. A translational movement and a corresponding force can be transmitted by force-locking or friction-locking between the rod coupling and the proximal end of the transmission rod. A pressure force or pushing force in the distal direction can also be transmitted by form-locking to the proximal end of the transmission rod.

If the proximal end of the transmission rod has a non-constant cross-section in the area foreseen for an arrangement in the rod coupling, a translational movement and a corresponding force can be transmitted alternatively or in addition in form-locked manner between the rod coupling and the proximal end of the transmission rod. In particular, the proximal end of the transmission rod comprises one or more indentations and/or recesses in which the rod coupling can engage.

A handling device as described here also comprises, in particular, a slide bar, which can slide in the handling device between a predetermined distal assembly position and a predetermined proximal working position, such that the slide bar is configured and positioned to be held in the predetermined proximal working position by a proximal end of a shaft that is blocked in the shaft coupling.

The slide bar can slide in particular along a straight line that is parallel to the longitudinal axis of a proximal end of a transmission rod that is inserted or to be inserted into the handling device. The slide bar can produce additional degrees of freedom in designing or building the handling device and a shaft and transmission rod that are intended to be used with the handling device. In particular, the slide bar can bridge a distance between the proximal end of a shaft inserted into the handling device and the distal end of the rod coupling or another site upon which the slide bar acts on the slide coupling. Thereby, in simple and reliable manner, the slide bar can make it possible that, with the shaft locked or blocked in the handling device, the position of the rod coupling is held in the working range in which the rod coupling holds the proximal end of the transmission rod.

In addition, as becomes clear hereinafter, in particular with reference to the embodiments, the slide bar can comprise or assume additional functions. Thus, the slide bar can make possible an especially compact structure for the handling device.

The slide bar comprises in particular a pass-through opening, which extends from the distal to the proximal side, such that the cross-section of the pass-through opening constantly varies in the direction from distal to proximal, at least in portions.

The cross-section of the pass-through opening becomes narrower, in particular, from the distal to the proximal side. At the distal side the pass-through opening accommodates the proximal end of a transmission rod, in particular in any desired orientation. In proceeding from distal to proximal, the cross-section of the pass-through opening varies in such a way that a proximal end of a transmission rod, which originally has any orientation within a predetermined solid angle, is rotated into a predetermined orientation in a movement from the distal to the proximal direction. For this purpose the cross-section of the pass-through opening varies, in particular continuously or in portions continuously.

The pass-through opening of the slide bar comprises, in particular, a glide surface, which is not parallel to the direction in which a shaft and a transmission rod are to be inserted into the handling device. In particular, several glide surfaces are provided. In particular, several glide surfaces are foreseen. Each glide surface can be flat or spiral-shaped in order to cause a rotation into a predetermined orientation or into one of several predetermined orientations during a movement of a proximal end of a transmission rod from distal to proximal in the pass-through opening.

For example, the slide bar comprises in the pass-through opening two flat glide surfaces, so that the pass-through opening narrows in a wedge-shape from distal to proximal. The distance between the two glide surfaces on the distal end of the pass-through opening is selected, in particular, in such a way that the proximal end of a transmission rod can be inserted into the pass-through opening in any desired orientation on the distal end. On the proximal end, the two glide surfaces comprise in particular a distance that is selected in such a way that a proximal end of a transmission rod can be fed entirely through the pass-through opening only in two predetermined orientations that are 180 degrees apart.

The pass-through opening can, alternatively, be configured at the distal end in such a way that the proximal end of a transmission rod can be inserted into the pass-through opening only in an orientation within one or more solid angles, such that a proximal end of a transmission rod with an orientation within one or more small, predetermined dead areas cannot be inserted into the pass-through opening.

Glide surfaces, in particular flat or wedge-shaped glide surfaces directed toward one another, can be easily producible means for automatic rotation of a proximal end of a transmission rod into a predetermined orientation that achieve a reliable effect along with low production costs.

With a handling device as described here, the slide bar can rotate around an axis, in particular with respect to the handling device, such that the slide bar in addition is configured to transmit torque onto a transmission rod coupled with the rod coupling.

In particular, the slide bar can rotate around a longitudinal axis of a proximal end of a shaft inserted into the handling device or of a proximal end of a transmission rod in the shaft. To transmit torque onto a transmission rod coupled with the rod coupling, the slide bar in particular on its proximal end is configured as form-locked with the proximal end of the foreseen transmission rod. For example, the proximal end of the transmission rod comprises a flattening with two parallel surfaces at a predetermined distance, and the slide bar comprises on its proximal end two opposite surfaces at the predetermined distance or a slightly greater distance.

The slide bar is coupled, in particular directly or indirectly, with a rotation wheel or other actuation device on the handling device, by means of which the slide bar and thereby a transmission rod of a shaft inserted into the handling device can be rotated or else torque can be transmitted onto it.

Several functions can thus be integrated into the slide bar, in particular automatic rotation of a proximal end of a transmission rod into a predetermined orientation, locking of the rod coupling and transmission of torque onto an inserted transmission rod. This integration or realization of several functions in the slide bar makes possible an especially simple, reasonably priced, compact and robust structure for the handling device.

With a handling device as described here, the rod coupling includes in particular a movable gripping jaw for holding a proximal end of a transmission rod, such that the rod coupling is configured in such a way that the gripping jaw, with the rod coupling in a predetermined assembly position, can receive or release a proximal end of a transmission rod and can hold a proximal end of a transmission rod in a predetermined range of working positions of the rod coupling.

The rod coupling includes in particular two or more symmetrically disposed gripping jaws. Alternatively, the rod coupling includes only one gripping jaw or one asymmetrical arrangement of gripping jaws. Each gripping jaw can pivot, in particular, around an associated axis between an assembly position and a holding position. With the gripping jaw in the assembly position or with the gripping jaws in assembly positions, a proximal end of a transmission rod can be inserted into the rod coupling and removed from it. With the gripping jaw in the holding position or with the gripping jaws in holding positions, a proximal end of a transmission rod can be held by the gripping jaw or jaws in a form-locked and/or force-locked or friction-locked connection.

In particular, the gripping jaw or gripping jaws are configured to include a claw or a portion with an enlarged cross-section on the proximal end of a transmission rod in order to form a form-locked connection with the proximal end of the transmission rod. In somewhat more general terms, the gripping jaw can comprise a concave area into which a corresponding convex area on the proximal end of the transmission rod can engage. Alternatively, the gripping jaw or jaws can be configured to engage into a tapering or a concave area on or close to the proximal end of the transmission rod in order to form a form-locked connection with the proximal end of the transmission rod. In addition, both the gripping jaw or gripping jaws and the proximal end of the transmission rod can each comprise a convex area (or several convex areas) and in each case a concave area (or several concave areas), such that in each case a convex area is configured on the gripping jaw in order to engage into a concave area on the proximal end of the transmission rod and such that in each case a convex area is configured on the proximal end of the transmission rod in order to engage into a concave area on the gripping jaw.

The handling device can, in addition, include a guide pin and a control groove, such that either the guide pin or the control groove is positioned on the gripping jaw and such that the guide pin engages into the control groove in order to hold the gripping jaw in different positions independently of the position of the rod coupling.

In particular, the guide pin and the control groove are configured and disposed in such a way that the gripping jaw, with the rod coupling in the assembly position, is pivoted away from the foreseen position of a proximal end of a transmission rod and is pivoted into positions in the predetermined working range toward the proximal end of the transmission rod and is in form-locked connection with the transmission rod. In particular, the control groove is positioned non-slidably on the handling device in the direction in which the rod coupling can slide while the guide pin is positioned on the gripping jaw.

The control groove can be rotatable with the entire rod coupling and, in some cases, with the slide bar, in particular around the longitudinal axis of a proximal end of a transmission rod that is inserted or to be inserted into the rod coupling. In the case of several gripping jaws, each gripping jaw in particular comprises one or more guide pins. The gripping jaw or each of several gripping jaws comprises, in particular, two opposite guide pins, which engage into control grooves placed opposite and running parallel.

With a handling device in which the rod coupling includes a movable gripping jaw to hold a proximal end of a transmission rod, and in which the slide bar can slide between a predetermined distal assembly position and a predetermined proximal working position, a surface area in particular is configured on the slide bar in order to form, with the slide bar in the predetermined proximal working position, a mechanical stop for the gripping jaw of the rod coupling, which restricts the predetermined working area.

In particular, a proximal front surface of the slide bar is configured as a stop. Alternatively another area of the surface of the slide bar, which is partly or completely oriented in the proximal direction, can be configured as a stop for a part of the rod coupling disposed proximally from the area.

The handling device is thus, in particular, configured in such a way that the gripping jaw of the rod coupling is contiguous with the surface area of the slide bar that is configured as a stop, when the slide bar is situated in its working position and the rod coupling is situated in the most distal position within the predetermined working range. In particular when the gripping jaw or jaws are disposed on the distal end of the rod coupling, the mechanical stop of the gripping jaws of the rod coupling can constitute a structurally simple and reliable solution on the slide bar.

A micro-invasive surgical instrument includes a handling device as described here, a shaft with a proximal end that is configured for detachable coupling with the handling device, and with a distal end that is mechanically connected or connectable with a tool, and a transmission rod to transmit at least either a force or torque from the handling device to the distal end of the shaft.

The shaft of the micro-invasive surgical instrument can be straight or curved, rigid or flexible. In the case of a curved or flexible shaft, the transmission rod is, in particular, pliable at least in some parts. The tool particularly includes a grasping, dissecting, biopsy or other type of forceps, a scissors or a needle holder with at least two straight or curved clamps, cutting edges or other jaw members, at least one of which is movable. Alternatively, the tool can include another active device, for example a manipulator with a finger or a finger-shaped device or an electrode in hooked shape or some other form. The transmission rod is particularly configured to transmit a tractive and/or pushing force to the tool on the distal end of the shaft. Alternatively or in addition, the transmission rod can be configured to transmit torque and a rotary movement to the tool. The proximal end of the transmission rod has, in particular, a shape that corresponds to a proximal end of a pass-through opening in the orientation device.

The proximal end of the shaft of the micro-invasive surgical instrument is configured in particular, in the predetermined position, to hold the rod coupling directly or indirectly in the predetermined working area.

With the characteristics and properties of the handling device and corresponding characteristics and properties of the shaft and transmission rod, as described here, a simple, rapid and reliable installation and efficient use of the micro-invasive surgical instrument are possible.

With the micro-invasive surgical instrument, in addition, the transmission rod can be configured to transmit torque from the handling device to the distal end of the shaft.

In particular, the tool on the distal end of the shaft can be rotated or turned around its longitudinal axis by means of torque transmitted by the transmission rod from the handling device to the distal end of the shaft. Rotation of the tool independently of the shaft is thereby possible. For example with a micro-invasive procedure with several instruments with cured shafts in a trocar, each individual tool can be turned independently of the orientation of the curved shaft on whose end the tool is mounted.

The proximal end of the shaft is configured, in particular, in the predetermined blockable position, to hold the rod coupling directly or indirectly in the predetermined working range.

With the micro-invasive surgical instrument, the transmission rod, in particular, is further configured to transmit torque from the handling device to the distal end of the shaft.

In particular, the transmission rod is configured to transmit torque from the handling device to a tool on the distal end of the shaft. The transmission rod is thus rigid or inelastic, in particular with respect to pressure or tractive impacts in the longitudinal direction and with respect to torsion. At the same time the transmission rod can be pliable, in particular in the case of an at least partly curved shaft.

With a micro-invasive surgical instrument as described here, the tool and the distal end of the shaft can be detachably mechanically coupled with one another, such that tool, shaft and transmission rod are configured in such a way that the tool is locked on the distal end of the shaft when the position of the rod coupling coupled with the proximal end of the transmission rod is situated in the predetermined working range.

The detachable connection between tool and shaft can improve, or in fact basically make possible, the cleaning of the instrument. The locking of the tool on the distal end of the shaft, if the position of the rod coupling coupled with the proximal end of the transmission rod is situated in the predetermined working range, can make possible a complete dismantling of the instrument merely by releasing the blocking of the shaft on the handling device. This can markedly simplify or improve the handling of the instrument, in particular its dismantling and assembly.

A micro-invasive surgical instrument as described here includes in particular a tool on the distal end of the shaft so that the tool includes a curved jaw member.

In particular, the tool includes two or more curved jaw members. As long as a curved jaw member can be pivoted around a pivot axis, it is curved in particular in a plane perpendicular to the pivot axis or in a plane parallel to the pivot axis or in both directions.

Arched or even screw-shaped curved clamps, cutting edges or other jaw members of micro-invasive surgical instruments are especially suited for some applications. With an application of a tool with two curved jaw members, however, contrary to a tool with two equal or similar, straight or essentially straight jaw members, a rotation by more than 90 degrees (up to 180 degrees) can be required to align the tool correctly in relation to an object. Rotatability of a tool with one or more curved jaw members around a longitudinal axis of a shaft of a tool can therefore be especially advantageous.

BRIEF DESCRIPTION OF THE DRAWINGS

Embodiments are presented in greater detail hereinafter with reference to the attached drawings, which are as follows.

FIG. 1 shows a schematic depiction of a micro-invasive surgical instrument.

DETAILED DESCRIPTION OF THE INVENTION

Figure 1:
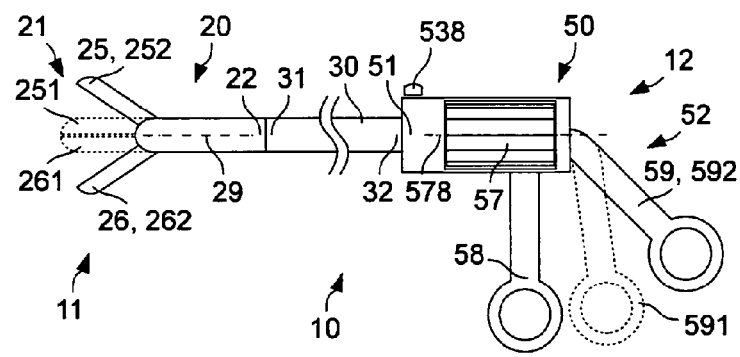
FIG. 1 is

FIG. 1 shows a schematic depiction of a micro-invasive surgical instrument 10 with a distal end 11 and a proximal end 12. The micro-invasive surgical instrument 10 includes a tool 20, a shaft 30 and a handling device 50. On the distal end 21 the tool 20 comprises a first movable jaw member 25 and a second movable jaw member 26. The jaw members 25, 26 are shown in FIG. 1 in firm outline in open positions 252, 262 and in dotted lines in closed positions 251, 261. The jaw members 25, 26 can each be straight or essentially straight or can be curved in the direction perpendicular to the plane of projection of FIG. 1 and/or—contrary to the depiction in FIG. 1—in the plane of projection of FIG. 1.

The proximal end 22 of the tool 20 is detachably mechanically coupled with a distal end 31 of the shaft 30. The shaft 30 is shown strongly foreshortened in FIG. 1 and straight for the sake of simplicity. Contrary to the depiction in FIG. 1, the shaft 30 can be level or spatially curved. With a shaft 30 that is within a plane or—even more advantageous for a few applications—spatially curved in shape, the micro-invasive surgical instrument 10 can be suited especially for surgical procedures in which the endoscope and one or more instruments are inserted simultaneously into a body cavity through a single access way.

The proximal end 32 of the shaft 30 is detachably mechanically coupled with the distal end 51 of the handling device 50. The handling device 50 comprises a rotary wheel 57, a first gripping member 58 and a second gripping member 59 for handling the micro-invasive surgical instrument 10. The rotary wheel 57 is provided to control a rotation of the tool 20, in particular the jaw members 25, 26, around a longitudinal axis 29. In the example shown in FIG. 1, the rotary wheel 57 can rotate around an axis 578 that is simultaneously the longitudinal axis of the shaft 30 on its proximal end 32. Alternatively, the axis 578 can be parallel to the longitudinal axis of the shaft 30 on its proximal end 32. In addition, the rotary wheel 57 comprises a surface structure that allows reliable operation or actuation even with gloves, for example the indicated pin in the axial direction. The gripping members 58, 59 in particular—contrary to the strongly stylized shape shown in FIG. 1—are positioned and formed in such a way that medical staff can grip and move the two gripping members 58, 59 in relation to one another with one hand without little fatigue.

At least one of the two gripping members 58, 59 is movable in relation to the other components of the handling device 50. In the example shown in FIG. 1, the first gripping member 58 is rigidly positioned and the second gripping member 59 is movably positioned. The second gripping member 59, in particular, is movable between the first working position 591 shown in dotted lines in FIG. 1 and a second working position 592 indicated in firm lines in FIG. 1. The second gripping member 59 of the handling device 50 is mechanically coupled with the jaw members 25, 26 of the tool 20 in such a way that the jaw members 25, 26 happen to be in their closed positions 251, 261 when the second gripping member assumes its first working position 591, and that the jaw members 25, 26 happen to be in their open positions 252, 262 when the second gripping member 59 assumes its second working position 592.

Figure 2:
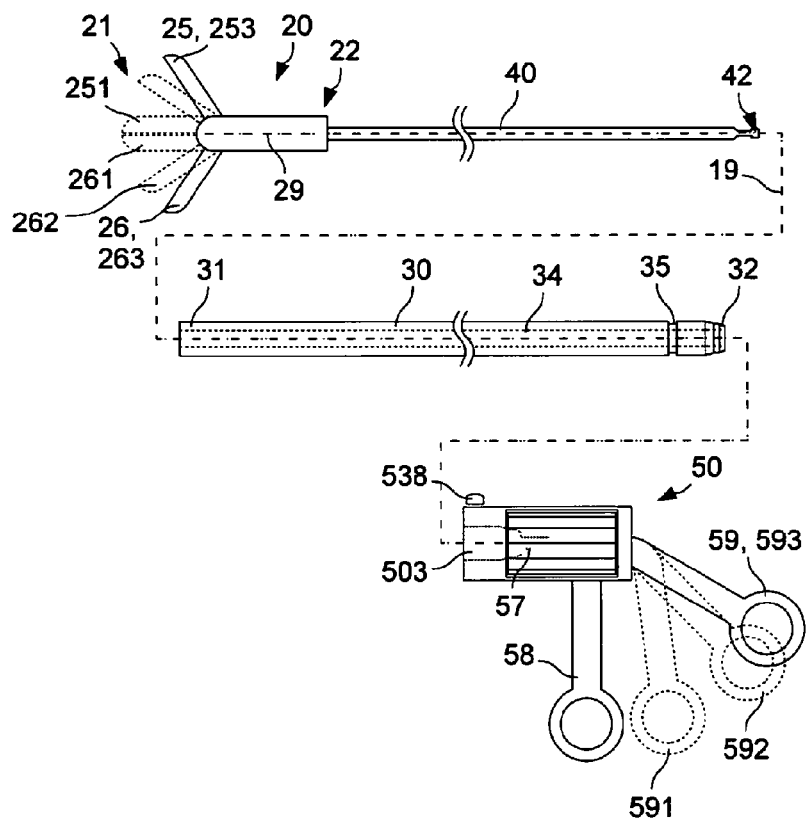
FIG. 2 shows a schematic depiction of the micro-invasive surgical instrument from FIG. 1 in dismantled form.

FIG. 2 shows a schematic depiction of components of the micro-invasive surgical instrument 10 described above with reference to FIG. 1, which can be installed and/or assembled to form an instrument without use of a tool. Likewise, the micro-invasive surgical instrument 10 can be dismantled without a tool into the components illustrated separately in FIG. 2. The broken line 19 that runs through the entire FIG. 2 indicates how these components are to be assembled.

The tool 20 is, in particular, durably connected with a transmission rod 40 that is provided to transmit a force and torque from the handling device 50 to the tool 20. The distal end of the transmission rod 40, which is not shown in FIG. 2, is coupled with the jaw members 25, 26 in such a way that a movement of the transmission rod 40 parallel to the longitudinal axis 29 of the tool 20 causes a synchronous movement of the jaw members 25, 26.

Bayonet coupling devices, not shown in FIG. 2, as well as a locking device coupled with the transmission rod 40 are provided on the proximal end 22 of the tool 20 and on the distal end 31 of the shaft 30. The jaw members 25, 26 are shown in FIG. 2 in firm outline in fully open positions 253, 263 and in dotted lines in the closed and open positions 251, 252, 261, 262 already described above with reference to FIG. 1. If the jaw members 25, 26 happen to be the fully open positions 253, 263, the locking device that is coupled with the jaw members 25, 26 and the distal end of the transmission rod 40 and not shown in FIG. 2 is inactive. In this condition the transmission rod 40 can be inserted in a channel 34 foreseen for the transmission rod 40 in the shaft 30, and the proximal end 22 of the tool and the distal end 31 of the shaft can be detachably mechanically connected or coupled together by the bayonet coupling devices not shown in FIG. 2. In addition, in this unlocked condition a mechanical coupling of the proximal end 22 of the tool 20 and the distal end 31 of the shaft 30 can be released by the bayonet coupling devices that are not shown in FIG. 2.

If the jaw members 25, 26 are in the closed positions 251, 261, in the open positions 252, 262 or in positions situated in between, then the locking device that is coupled with the distal end of the transmission rod 40 and directly with the jaw members 25, 26 is situated in a working position or in a position inside a working range. In the working position or in the positions within the working range, the mechanical coupling of the proximal end 22 of the tool 20 is locked with the distal end 31 of the shaft 30 by the bayonet coupling devices not shown in FIG. 2. If the mechanical connection or coupling of the tool 20 and shaft 30 is locked, the tool 20 and shaft 30 cannot be separated from one another, or not necessarily without disturbance.

Instead of the bayonet coupling devices, the proximal end 22 of the tool 20 and the distal end 31 of the shaft 30 can comprise other coupling devices. In this case too, a locking device is provided on the tool 20 that locks the mechanical connection of the tool 20 and shaft 30 when the jaw members 25, 26 are found in the fully open positions 253, 263.

If the transmission rod 40 is inserted in the channel 34 of the shaft 30 and the proximal end 22 of the tool 20 is mechanically connected or coupled with the distal end 31 of the shaft 30, the proximal end 32 of the shaft 30 with the proximal end 42 of the transmission rod 40 that projects outward with respect to the proximal end 32 of the shaft 30 can be inserted in the handling device 50. For this purpose the handling device 50 comprises a recess 503 as indicated by a dotted line in FIG. 2.

To insert the proximal end 32 of the shaft 30 and the proximal end 42 of the transmission rod 40 in the handling device 50, the second gripping member 59 is first brought into a coupling position 593 as shown in unbroken lines in FIG. 2. If the second gripping member 59 is in the coupling position 593, then a rod coupling inside the handling device 50 but not shown in FIG. 2 is found in a coupling position in which it can receive or release the proximal end 42 of the transmission rod 40. If the proximal end 42 of the transmission rod 40 is inserted entirely in the handling device 50, the rod coupling that is inside the handling device 50 but is not shown in FIG. 2 is mechanically connected or coupled with the proximal end 42 of the transmission rod 40. In so doing, the second gripping member 59, depending on the positions of the jaw members 25, 26 (closed positions 251, 261, open positions 252, 262 or in between), moves into the first working position 591, the second working position 592 or a position between the first working position 591 and second working position 592.

If the proximal end 32 of the shaft 30 is inserted completely into the handling device 50, a bolt that is not shown in FIG. 2 grips in a surrounding groove 35 close to the proximal end 32 of the shaft 30, thus locking the proximal end 32 of the shaft 30 in a foreseen position in the handling device 50. Because of the locking of the proximal end 32 of the shaft 30 in the handling device 50, the mechanical coupling of the proximal end 42 of the transmission rod 40, with the rod coupling that is not shown in FIG. 2, is also indirectly locked in the interior of the handling device 50.

After the locking of the proximal end 32 of the shaft 30 in the handling device 50, and indirectly of the proximal end 42 of the transmission rod 40 in the handling device 50 in the rod coupling not shown in FIG. 2, the micro-invasive surgical instrument 10 is configured as shown in FIG. 1. By moving the second gripping member 59 in relation to the first gripping member 58 between the two working positions 591, 592, the jaw members 25, 26 can be moved between the closed positions 251, 261 and the open positions 252, 262. By rotating the rotary wheel 57 around the axis 578, the jaw members 25, 26 can be rotated around the longitudinal axis 29 of the tool 20.

Contrary to the depictions in FIGS. 1 and 2, the shaft 30 can comprise, close to its proximal end 32, a second rotary wheel that is positioned close to the distal end 51 of the handling device 50 if the proximal end 32 of the shaft 30 is inserted into the handling device 50. The shaft 30 can be rotated around the longitudinal axis of the proximal end 20 of the shaft 30 by means of this rotary wheel, which is not shown in FIGS. 1 and 2. This is particularly significant when the shaft 30 is curved, contrary to the depictions in FIGS. 1 and 2. In this case the curved shaft 30 and the tool 20 can be rotated independently of one another on the distal end 31 of the curved shaft 30.

Through pressure on the unlocking button 538, the bolt, not shown in FIG. 2, can be pushed against the force of a spring and can be disengaged from the groove 35 on the shaft 30. Then the proximal end 32 of the shaft 30 can be removed from the handling device 50. At the same time, the locking of the proximal end 42 of the transmission rod 40, on the rod coupling in the handling device 50 that is not shown in FIGS. 1 and 2, is also released.

Instead of one or—as shown in FIGS. 1 and 2—two movable jaw members 25, 26, the tool 20 can comprise a different active device, in particular a manipulator, for example a finger-shaped manipulator, or an electrode, for example a hook-shaped electrode.

Figure 3:
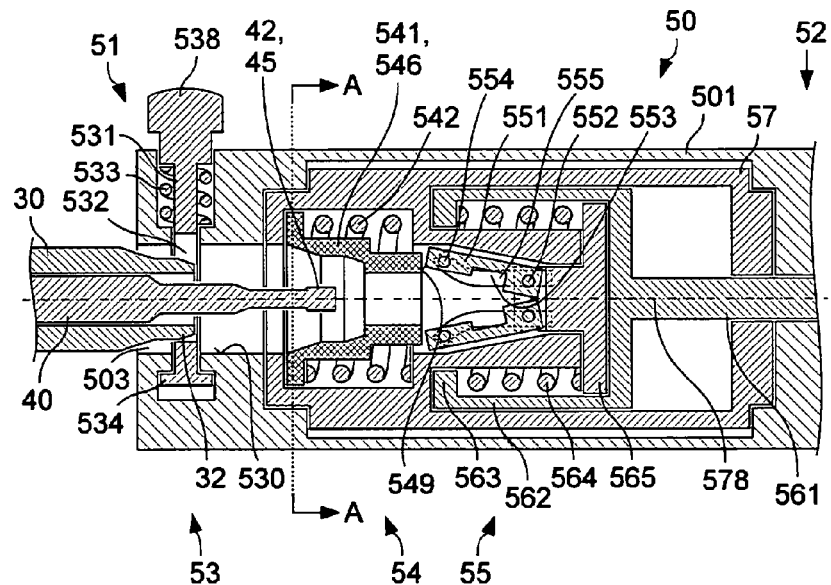
FIG. 3 shows a schematic depiction of a handling device.

FIG. 3 shows a schematic depiction of a section along an embodiment of the handling device 50 of the micro-invasive surgical instrument presented above with reference to FIGS. 1 and 2. The illustrated sectional plane is parallel to the planes of projection of FIGS. 1 and 2 and contains the axis 578 already indicated in FIGS. 1 and 2. The gripping members 58, 59 shown in FIGS. 1 and 2 are not included in FIG. 3.

The handling device 50 includes a housing 501 with the recess 503 that extends from the distal end 51 of the handling device 50 and was already indicated in FIG. 2. The surface of the recess 503 is, in particular, configured essentially as a cylindrical guide surface 530 symmetrical to the axis 578. A proximal end 32 of a shaft 30 and a proximal end 42 of a transmission rod 40 positioned in the shaft 30 are shown in FIG. 3 partly inserted in the recess 503.

The complete insertion of the proximal end 32 of the shaft 30 and of the proximal end 42 of the transmission rod 40 into the handling device 50, the locking of the shaft 30 on the handling device 50 and the mechanical coupling of the proximal end 42 of the transmission rod 40 with elements of the handling device 50 are described below with reference to FIGS. 6 through 8. First, with reference to FIG. 3, only the components or elements of the handling device 50 are described.

A few components or elements of the handling device 50, which are each presented in FIGS. 3 and 6 through 8 as in a single piece because they each constitute rigid mechanical units in themselves in the handling device 50, can each be composed of several form-locked, force-locked or firmly bonded joined elements, contrary to the illustrations, for example for technical manufacturing reasons.

The handling device 50 includes a shaft coupling 53 close to the distal end 51. The shaft coupling 53 is configured by the guide surface 530 and a locking unit to lock or block the shaft 30 in the handling device 50. The locking device includes a bolt 531 that extends essentially perpendicularly to the axis 578 and can slide in linear manner perpendicularly to the axis 578 within a predetermined area.

At one end the bolt 531 comprises a collar 534 in a hollow space in the housing 501 of the handling device 50, and the shape of the collar 534 and the shape of the hollow space restrict the linear slidability of the bolt 531. On the other end the bolt 531 comprises an unlocking button 538, which extends with respect to the outer contour of the housing 501 of the handling device 50. The bolt 531 comprises an opening 532, which is adapted to the outer contour of the cross-section of the shaft 30. A spring 533 between an indentation on the housing 501 of the handling device 50 and an indentation on the bolt 531 pushes the bolt 531 into the position shown in FIG. 3.

By pressure on the unlocking button 538 or by the impact of a conical portion on the shaft 30 on the border of the opening 532 in the bolt 531, the bolt 531 can be pushed in linear manner against the force of the spring 533 all the way to a position in which the border of the opening 532 in the bolt 531 no longer protrudes into the recess 503. In this position of the bolt 531, the shaft 30 can be inserted into the recess 503 or removed from it.

The handling device 50 further includes a control and orientation device 54, designated hereinafter as orientation device, and a rod coupling 55 inside the essentially drum-shaped pivot wheel 57. The orientation device 54 and the rod coupling 55 are configured to be rotated together with the pivot wheel 57 and the axis 578. The orientation device 54 and rod coupling 55 are therefore rigidly connected with the pivot wheel 57 with respect to rotation around the axis 578. Both the orientation device 54 and the rod coupling 55, however, can be slid inside the handling device and in relation to the pivot wheel 57 in axial direction or parallel to the axis 578, each within a predetermined area.

The orientation device 54 includes a slide bar 541, which in FIG. 3 is shown in a distal installation position 546. Between a collar of the slide bar 541 and the pivot wheel 57, a spring 542 is positioned that holds the slide bar 541 elastically in the installation position 546. The slide bar 541 and pivot wheel 57, in particular, on the proximal end of the slide bar 541 in the surrounding of a proximal front surface 549 of the slide bar 541, comprise surfaces that are adjacent with one another and are not rotation symmetrical to the axis 578. The slide bar 541 is thereby held in a predetermined orientation in relation to the pivot wheel 57, independently of its position in the axial direction with respect to rotation around the axis 578.

The rod coupling 55 includes two gripping clamps 551 that are positioned symmetrically to the axis 578 and that are jointedly affixed by joints 552 to a force transmission component 565. Each gripping clamp 551 comprises a recess 553 with a shape that corresponds to the form of a claw 45 on the proximal end 42 of the transmission rod 40. In addition, each gripping clamp 551 comprises a guide pin 554 whose axis is perpendicular to the sectional plane of FIG. 3. Every end of each of the guide pins 554 engages in each case in an associated control groove 555 in the pivot wheel 57. Besides the two control grooves 555 shown in FIG. 3, two control grooves not shown in FIG. 3 behind the sectional plane of FIG. 3 are foreseen on the pivot wheel 57 and are mirror symmetrical to the control grooves 555 shown in FIG. 3 with respect to the sectional plane of FIG. 3. The control grooves 555 are curved at least in portions. In a linear sliding of the joints 552 of the gripping clamps 551 parallel to the axis 578, the control grooves 555 cause pivotal movements of the gripping clamps 551, which are described below with reference to FIGS. 6 through 8.

Inside the pivot wheel 57, in addition, a rod 561 and a beaker-shaped component 562 are positioned. The rod 561 and the beaker-shaped component 562 are rigidly interconnected and can slide parallel to the axis 578 inside the pivot wheel 57. A pressure spring 564 is positioned between a collar 563 of the beaker-shaped component 562 pointing radially inward and a collar of the force transmission component 565 pointing radially outward. The pressure spring 564 restricts a tractive force that can be transmitted from the rod 561 via the beaker-shaped component 562, the pressure spring 564, the force transmission component 565 and the gripping clamps 551 to a proximal end 42 of a transmission rod 40 that is coupled with the gripping clamps 551.

The proximal end of the rod 561, which is not shown in FIG. 3, is—for example by means of a connection rod— coupled with the second gripping member 59, described above with reference to FIGS. 1 and 2, in such a way that a pivot movement of the second gripping member 59 causes a linear movement of the rod 561 and of the rod coupling 55 parallel to the axis 578.

Figure 4:
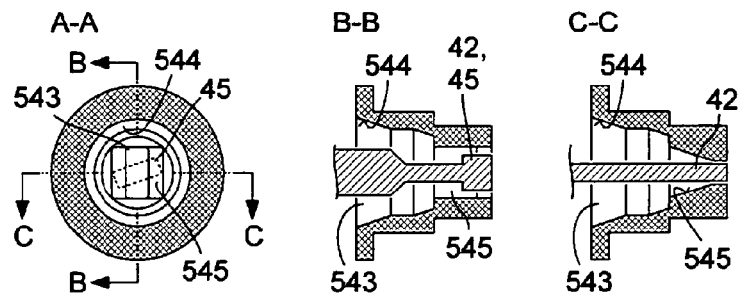
FIG. 4 shows a schematic depiction of an orientation device.
Figure 5:
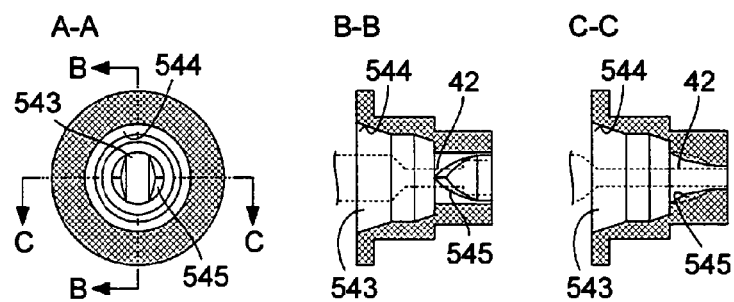
FIG. 5 shows a schematic depiction of an additional orientation device.

Before a closer discussion of the functioning of the rod coupling 55 with reference to FIGS. 6 through 8, two different embodiments of the slide bar 541 are described with reference to FIGS. 4 and 5. FIGS. 4 and 5 each show a section along the sectional plane A-A indicated in FIG. 3 at the left, and sections along the planes B-B and C-C in the center and at right, which are indicated in FIGS. 4 and 5 at the left in depictions of the section along the plane A-A. The sectional plane A-A is perpendicular to the axis 578 shown in FIG. 3. The sectional planes B-B and C-C each contain the axis 578. All sectional planes A-A, B-B and C-C are perpendicular to one another.

Both embodiments of the slide bar 541 illustrated in FIGS. 4 and 5 comprise a pass-through opening 543. In a distal portion shown in each case at the left in FIGS. 3 through 5, the surface of the pass-through opening 543 is configured as a partly conical support surface 544 for the proximal end 32 of the shaft 30. The support surface 544 is rotation symmetrical or essentially rotation symmetrical to the axis 578 and adapted to the shape of the proximal end 32 of the shaft 30 shown in FIG. 3.

In the embodiment of the slide bar 541 illustrated in FIG. 4, the pass-through opening 543 comprises in a proximal portion two flat and essentially rectilinear gliding surfaces 545, which face one another in wedge shape running from distal to proximal. The gliding surfaces 545 form with their distal edges an approximately square cross-section of the pass-through opening 543. With their proximal edges the gliding surfaces 545 form a narrow rectilinear cross-section, which is adapted to the cross-section of the claw 45 of the proximal end 42 of the transmission rod 40 illustrated in FIG. 3.

Shown in broken lines at the left in FIG. 4, in the section along the plane A-A, is the cross-section of the claw 45 on the proximal end 42 of the transmission rod in the orientation illustrated in FIG. 3. This orientation of the proximal end 42 and of the claw 45 does not correspond to the orientation determined by the cross-section of the pass-through opening 543 on the proximal edges of the glide surfaces 545. In the center and at right in FIG. 4, in the sections along the planes B-B and C-C, the proximal end 42 of the transmission rod is shown with the claw 45 in the orientation that is determined by the cross-section of the pass-through opening 543 at its proximal end.

In the section along the plane B-B, it can be recognized that the proximal end 42 of the transmission rod 40, in particular the claw 45, is not narrowly contained in the direction parallel to the sectional plane B-B and perpendicular to the axis 578. In the section along the plane C-C, it can be recognized that the proximal end 42 of the transmission rod 40 is contiguous with the slide bar 541 in the direction parallel to the sectional plane C-C- and perpendicular to the axis 578, thus determining the orientation of the proximal end 42 of the transmission rod 40. At the right in FIG. 4, in the section along the plane C-C, it can be recognized that the transmission rod 40 is flattened in a large area adjoining the proximal end 42 to allow it to be pushed even farther in the proximal direction, starting from the position with respect to the slide bar 541 as shown in the center and at right in FIG. 4.

FIG. 5 shows an alternative embodiment of the slide bar 541 in which the cross-section of the pass-through opening 543 of the slide bar 541 is modified in a proximal area from a circular to a rectilinear shape. Contrary to the embodiment in FIG. 4, four glide surfaces 545 are provided, which are not rectilinear and not level. The glide surfaces 545, similarly as in the embodiment in FIG. 4, in inserting a proximal end 42 of a transmission rod 40 from the distal to the proximal direction, cause a rotation of the transmission rod from a freely chosen original orientation to an orientation determined by the slide bar 541. To allow the glide surfaces 545 to be displayed also in sections B-B and C-C, FIG. 5 depicts the contours of the transmission rod 40 merely in broken lines.

Figure 6:
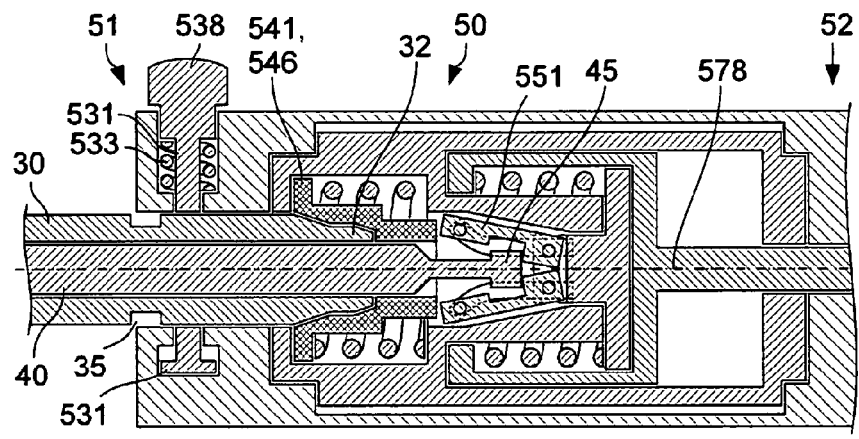
FIG. 6 shows an additional schematic depiction of the handling device from FIG. 3.
Figure 7:
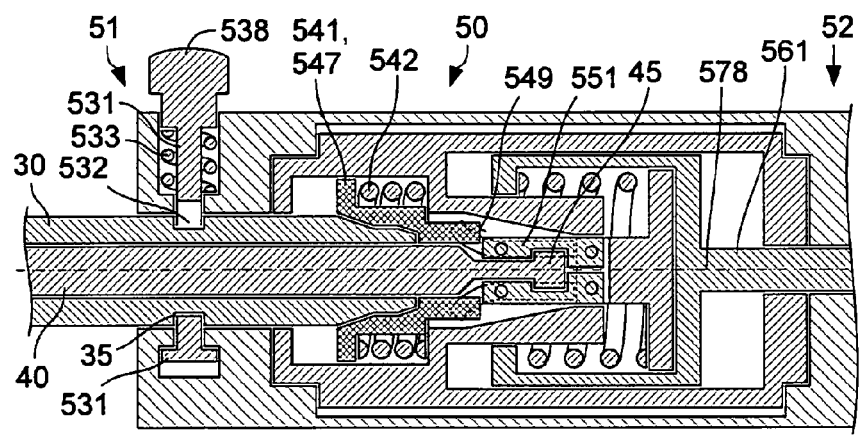
FIG. 7 shows an additional schematic depiction of the handling device from FIG. 3.
Figure 8:
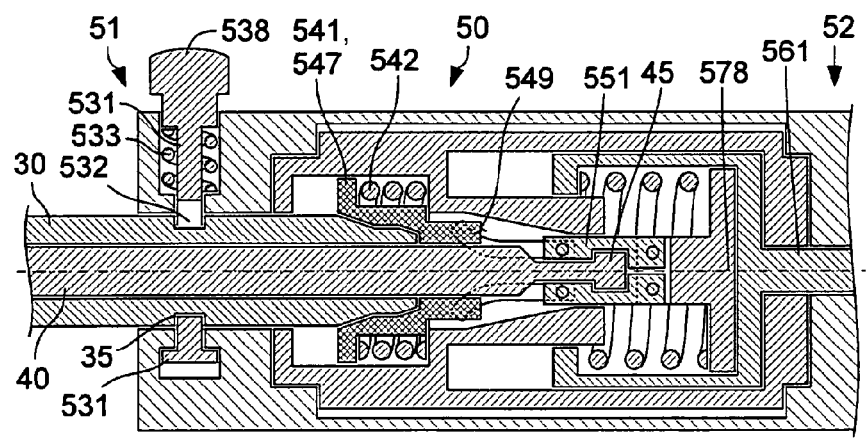
FIG. 8 shows an additional schematic depiction of the handling device from FIG. 3.

FIGS. 6, 7 and 8 show schematic depictions of the handling device 50, with the shaft 30 and transmission rod 40 in other positions with respect to the handling device 50. The sectional planes depicted in FIGS. 6, 7 and 8 correspond to the sectional plane of FIG. 3. To avoid cluttering FIGS. 6 through 8, reference numbers are displayed only for the most important characteristics.

In the situation illustrated in FIG. 6, the shaft 30 and transmission rod 40 are inserted so far into the handling device 50 that the proximal end 32 of the shaft 30 is contiguous with the slide bar 541. Upon sliding the proximal end 32 of the shaft 30 into the handling device 50, the bolt 531 upon touching a conical portion of the shaft 30 with the edge of the opening 532 in the bolt 531, was pushed against the force of the spring 533 perpendicular to the axis 578 into the position shown in FIG. 6.

The claw 45 on the proximal end 42 of the transmission rod 40 is already situated between the gripping clamps 551, which however are still found in an opened installation position.

In the situations shown in FIGS. 7 and 8, the shaft 30 is completely pushed into the handling device 50. The bolt 531 engages in the surrounding groove 35, already visible in FIG. 6, on the outermost surface of the shaft 30. By the spring 533, the bolt 531 is held in this position locking the shaft 30. Locking by the bolt 531 can be released only by pressure on the unlocking button 538. With the shaft 30 in the locked position shown in FIGS. 7 and 8, the slide bar 541 is pushed against the force of the spring 542 into its working position 547 and is held there by the shaft 30.

The situations shown in FIGS. 7 and 8 are distinguished by the fact that the rod 561, the rod coupling 55 and the transmission rod 40 are found in different positions. In particular, in the situation illustrated in FIG. 7, the jaw members 25, 26 shown in FIG. 1 are situated in their open positions 252, 262 and the second gripping member 59 is in the second working position 592. In the situation shown in FIG. 8, the jaw members 25, 26 shown in FIG. 1, in particular, are situated in their closed positions 251, 261 and the second gripping member 59 is situated in its first working position 591.

It can be recognized in FIG. 7 that the gripping clamps 551 are contiguous with the proximal front surface 549 of the slide bar 541. The slide bar 541 or its proximal front surface 549 thus forms a mechanical stop for the gripping clamps 551. The gripping clamps 551 therefore cannot be pushed farther in the distal direction with respect to their position shown in FIG. 7. The gripping clamps 551 thereby remain controlled by the control grooves 555, in which the guide pins 554 of the gripping clamps 551 engage (see also FIG. 3) in the closed working positions shown in FIGS. 7 and 8. In the closed working positions shown in FIGS. 7 and 8, the gripping clamps hold the claw 45 on the proximal end 42 of the transmission rod 40 in form-locked connection and with little play. Only after unlocking the shaft 30 by pressure on the unlocking button 538 can the shaft 30, the slide bar 541 and thus also the gripping clamps 551 be pushed so far in the distal direction that the gripping clamps 551, controlled by the control grooves 555, reach the installation positions shown in FIG. 6 and release the claw 45.

A further consequence of the mechanical stop of the gripping clamps 551 on the proximal front surface 549 of the slide bar 541 is that the transmission rod 40 held by the gripping clamps 551 cannot be pushed so far in the distal direction that the jaw members 25, 26 reach the fully open positions 253, 263 shown in FIG. 2. Thus, as shown above with reference to FIG. 2, the tool 20 likewise cannot be separated from the distal end 31 of the shaft 30.

In the embodiment presented with reference to FIGS. 3 through 8, the slide bar 541 comprises several functions. One function of the slide bar 541 is, during the insertion of the proximal end 42 of the transmission rod 40 into the handling device 50, to rotate the proximal end 42 of the transmission rod 40 into a predetermined orientation. An additional function of the slide bar 541 consists in restricting the slidability of the rod coupling 55 and of the transmission rod 40 in the distal direction when the shaft 30 is locked by means of the bolt 431 in the handling device 50. Restriction of slidability of the rod coupling 55 by the slide bar 541 causes a locking of the rod coupling 55 in the condition shown in FIGS. 7 and 8 in which the rod coupling 55 holds the proximal end 42 of the transmission rod 40. In addition, restriction of slidability of the rod coupling by the slide bar 541 also has the effect that the transmission rod 40 coupled with the rod coupling 55 cannot be pushed so far in the distal direction that the locking of the mechanical coupling, described above with reference to FIGS. 1 and 2, could be released by the tool 20 and the shaft 30.

Figure 9:
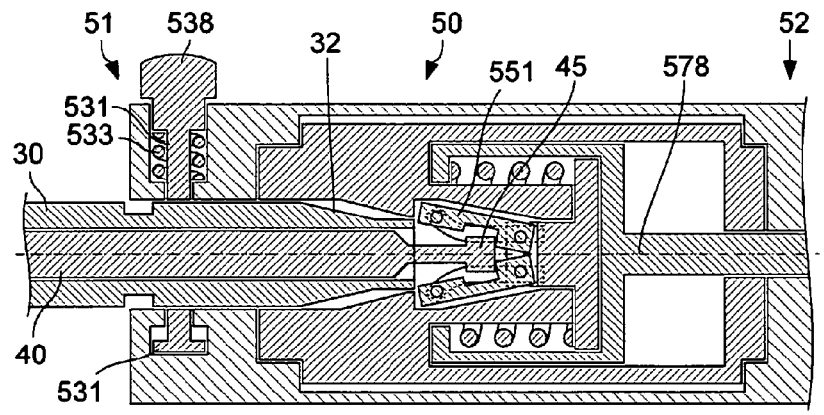
FIG. 9 shows a schematic depiction of an additional handling device.
Figure 10:
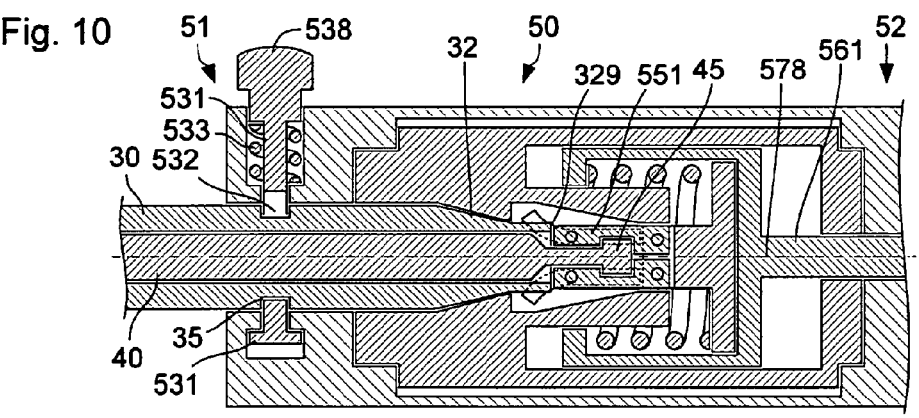
FIG. 10 shows another schematic depiction of the handling device from FIG. 9.
Figure 11:
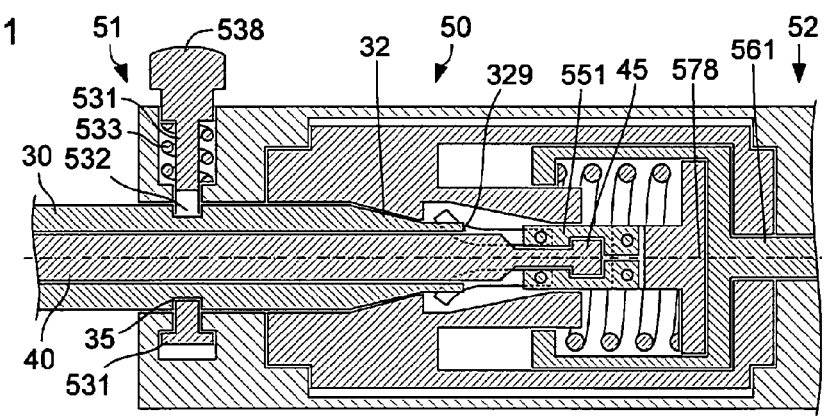
FIG. 11 shows another schematic depiction of the handling device from FIGS. 9 and 10.

FIGS. 9 through 11 show an alternative embodiment of the handling device 50, which resembles in some features the handling device 50 presented above with reference to FIGS. 3 through 8. FIGS. 9 through 11 show sections along sectional planes that correspond to the sectional planes of FIGS. 3 and 6 through 8. The situations shown in FIGS. 9, 10 and 11 correspond to the situations illustrated in FIGS. 6, 7 and 8. In particular, FIG. 9 shows the shaft 30 still not quite completely inserted into the handling device 50 and accordingly still not yet locked. In the situations shown in FIGS. 10 and 11, the shaft 30 is completely inserted into the handling device 50 up to a stop constituted by the rotation wheel 57 of the handling device 50 and is locked by the bolt 531. Alternatively, in a departure from the depiction in FIGS. 7 and 8, the housing 501 of the handling device 50 constitutes a mechanical stop for the shaft 30.

The handling device 50 shown in FIGS. 9 through 11 is distinguished from the embodiment presented above with reference to FIGS. 3 through 8 in particular in that no control or orientation device is foreseen. Instead, the handling device 50 and the shaft 30, in particular the proximal end 32 of the shaft 30, are configured in such a way that, with the shaft 30 in the locked position shown in FIGS. 10 and 11, a proximal front surface 329 on the proximal end 32 of the shaft 30 acts as a stop for the gripping jaws 551. Similarly as with the example presented above with reference to FIGS. 3 through 8, the gripping jaws 551 are thus locked in the working positions shown in FIGS. 10 and 11, in which they hold the claw 45 form-locked on the proximal end 42 of the transmission rod 40.

In addition, because of the stop for the gripping jaws 551 formed by the proximal end 32 of the shaft 30, the transmission rod 40 held by the gripping jaws 551 cannot be slid so far in the distal direction that the jaw members 25, 26 shown in FIGS. 1 and 2 could reach the fully opened positions 253, 263 shown in FIG. 2. Thus, simultaneously, the mechanical connection between the tool 20 and the distal end 31 of the shaft 30 is locked when the shaft 30 is held by the bolt 531 in the predetermined position in the handling device 50. In other words, the proximal end 32 of the shaft 30 locked in the handling device 50 locks the coupling of the rod coupling 55 with the proximal end 42 of the transmission rod 40 and the mechanical connection between the tool 20 and the distal end 31 of the shaft 30 by direct restriction of the ability of the rod coupling 55 to slide on the working area, which extends from the position shown in FIG. 10 all the way to the position shown in FIG. 11.

In the embodiments described above, the transmission rod 40 is configured both to transmit a translational movement in a direction parallel to the shaft 30 or to its longitudinal axis and to a corresponding pulling and/or pushing force and to transmit a rotational movement and corresponding torque. A force acting in the longitudinal direction is transmitted by form-locking between the rod coupling 55 of the handling device 50 and the proximal end 42 of the transmission rod 40. For this purpose, in particular, the gripping clamps 551 of the rod coupling 55 enclose the claw 45 on the proximal end 42 of the transmission rod 40 and receive it in their recesses 553. A force acting in the longitudinal direction can, alternatively or in addition, be transmitted by force locking or frictional locking between the rod coupling 55 and the proximal end 42 of the transmission rod. In particular, a force acting in the longitudinal direction, because of force locking or frictional locking, can also be transmitted when the proximal end 42 of the transmission rod 40 in the area of the rod coupling 55 has a constant cross-section instead of the claw 45.

Contrary to the description provided above with reference to the drawings, the transmission rod 40 and rod coupling 55 can be configured only to transmit torque. This can be the case, in particular, when the tool 20 on the distal end 31 of the shaft 30 can rotate only around the longitudinal axis of the distal end 31 of the shaft 30 or around another axis. For example, the tool 20 includes a finger-shaped or other manipulator of an electrode in hook or loop form or in some other shape. In particular when only torque is to be transmitted between the transmission rod 40 and the rod coupling 55, the proximal end 42 of the transmission rod 40 can have a constant cross-section, contrary to the depictions in FIGS. 2 through 8.

What is claimed is:

1. A handling device for a micro-invasive surgical instrument comprising:
    a shaft coupling for detachably coupling a proximal end of a shaft to said handling device;
    a rod coupling adapted to slide in said handling device between a rod assembly position and a range of rod working positions for detachably coupling a non-rotation-symmetrical proximal end of a transmission rod, which is disposed in a predetermined orientation, to said handling device, said rod coupling being rotatable to transmit torque to said non-rotation-symmetrical proximal end of said transmission rod, said transmission rod being disposed in said shaft; and
    a slide bar adapted to slide inside said handling device between a distal assembly position and a proximal working position, said slide bar automatically orienting said non-rotation-symmetrical proximal end of said transmission rod into said predetermined orientation upon receiving said non-rotation-symmetrical proximal end of said transmission rod;

wherein said shaft coupling is configured to block said proximal end of said shaft in a predetermined position in which the proximal end of said shaft holds said rod coupling in said range of rod working positions;

wherein said proximal end of said shaft being blocked in said shaft coupling holds said slide bar in said proximal working position.

2. The handling device of claim 1, wherein said slide bar comprises a pass-through opening, said opening having a cross-section that varies, at least in portions, from a distal side of the opening to a proximal side of the opening.

3. The handling device of claim 2, wherein said distal side of said pass-through opening receives the proximal end of said transmission rod from said distal side to said proximal side, said cross-section of said pass-through opening rotating the proximal end of said transmission rod into said predetermined orientation.

4. The handling device of claim 1, wherein said slide bar is rotatable around an axis with respect to said handling device, said slide bar being adapted to transmit torque onto said transmission rod coupled with said rod coupling.

5. The handling device of claim 1 further comprising an actuation device disposed in said handling device and connected to said slide bar, said actuation device being adapted to transmit torque to said slide bar and said transmission rod.

6. The handling device of claim 1, wherein said rod coupling comprises a movable gripping clamp for coupling with said proximal end of said transmission rod; and wherein, with said rod coupling being in said rod assembly position, said gripping clamp is adapted to receive or release said proximal end of said transmission rod, and, with said rod coupling being in said range of rod working positions, said gripping clamp is adapted to hold said proximal end of said transmission rod.

7. The handling device of claim 6, wherein said movable gripping clamp comprises at least two gripping clamps disposed symmetrically to a longitudinal axis of said proximal end of said shaft.

8. The handling device of claim 6 further comprising a guide pin and a control groove, one of said guide pin and said control groove being positioned on said movable gripping clamp;

wherein said guide pin is adapted to engage in said control groove, said engagement holding said movable gripping clamp in one of a plurality of positions depending on the position of said rod coupling.

* * * * *